(12) United States Patent
Agyapong et al.

(10) Patent No.: US 6,837,882 B2
(45) Date of Patent: Jan. 4, 2005

(54) PROTECTION TAMPON AND METHOD OF MAKING

(75) Inventors: Raymond Kusi Agyapong, Cincinnati, OH (US); Roberto Hollander, Caracas (VE); David Joseph Caracci, Evendale, OH (US); Susan Rachelle Hill, Cincinnati, OH (US); Bruce Leslie Hayes, Cincinnati, OH (US); Fiona Marie Taylor, Cincinnati, OH (US); James Arthur Keighley, Wyoming, OH (US); Kevin Charles Strong, Auburn, ME (US)

(73) Assignee: The Procter & Gamble Company, Cincinnati, OH (US)

( * ) Notice: Subject to any disclaimer, the term of this patent is extended or adjusted under 35 U.S.C. 154(b) by 39 days.

(21) Appl. No.: 10/361,277

(22) Filed: Feb. 10, 2003

(65) Prior Publication Data

US 2003/0158533 A1 Aug. 21, 2003

Related U.S. Application Data

(60) Division of application No. 09/695,552, filed on Oct. 24, 2000, now Pat. No. 6,554,814, which is a continuation-in-part of application No. 09/309,467, filed on May 10, 1999, now Pat. No. 6,258,075.

(51) Int. Cl.[7] .............................. A61F 5/44; A61F 13/20
(52) U.S. Cl. .................. 604/904; 604/354; 604/385.17; 604/379
(58) Field of Search ................................ 604/354, 379, 604/385.01, 385.17, 385.18, 904

(56) References Cited

U.S. PATENT DOCUMENTS

| | | |
|---|---|---|
| 1,731,665 A | 10/1929 | Huebsch |
| 1,964,911 A | 7/1934 | Haas |
| 2,123,750 A | 7/1938 | Schulz |
| 2,412,391 A | 12/1946 | Crockford |
| 2,464,310 A | 3/1949 | Harwood |
| 2,566,190 A | 8/1951 | Greiner |
| 3,013,558 A | 12/1961 | Leupoid |
| 3,037,506 A | 6/1962 | Penksa |
| 3,058,469 A | 10/1962 | Crockford |
| 3,101,714 A | 8/1963 | Penska |

(List continued on next page.)

FOREIGN PATENT DOCUMENTS

| | | |
|---|---|---|
| DE | 296 15 883 U1 | 4/1997 |
| EP | 1 064 901 A2 | 1/2001 |
| GB | 2 225 949 A | 6/1990 |
| JP | 61-073317 | 5/1986 |
| WO | WO 00/61052 A1 | 10/2000 |

*Primary Examiner*—Larry I. Schwartz
*Assistant Examiner*—Michael G. Bogart
(74) *Attorney, Agent, or Firm*—Bridget D. Murray; Kevin C. Johnson

(57) ABSTRACT

A tampon showing improved leakage protection through improved expansion characteristics is disclosed. The tampons disclosed demonstrate these improved expansion characteristics particularly in the width dimension without introducing new drawbacks. Preferred tampons are described which are compressed to an initial size comparable to current tampons, but which expand to a width exceeding that achieved by current tampons. Such increased expansion is preferably accomplished without an increase in the total absorbency of the tampon. Tampons of various absorbencies are disclosed having increased total expansion in the width direction compared to current tampons. Additionally, tampons of various absorbencies which expand to a greater degree in the width direction under pressure are also disclosed. Tampons of various absorbencies which expand at a rate exceeding that achieved previously are also disclosed. Microwave conditioning of tampon pledgets following compression is disclosed as part of the tampon formation process.

6 Claims, 3 Drawing Sheets

U.S. PATENT DOCUMENTS

| | | | |
|---|---|---|---|
| 3,135,262 A | 6/1964 | Kobler | |
| 3,420,234 A | 1/1969 | Phelps | |
| 3,572,341 A | 3/1971 | Glassman | |
| 3,674,029 A | 7/1972 | Bates | |
| 3,732,866 A | 5/1973 | Accavallo | |
| 3,738,364 A | 6/1973 | Brien | |
| 3,854,481 A | 12/1974 | Messing | |
| 3,905,372 A | 9/1975 | Denkinger | |
| 3,948,257 A | 4/1976 | Bossak | |
| 3,965,905 A | 6/1976 | Schoenholz | |
| 3,995,636 A | 12/1976 | Murray | |
| 4,077,408 A | 3/1978 | Murray | |
| 4,217,900 A | 8/1980 | Wiegner | |
| 4,326,527 A | 4/1982 | Wollangk | |
| 4,536,178 A | 8/1985 | Lichstein | |
| 5,047,024 A | 9/1991 | Glassman | |
| 5,112,348 A | 5/1992 | Glassman | |
| 5,718,675 A | 2/1998 | Leijd | |
| 5,800,338 A | 9/1998 | Kollerup | |
| 6,039,716 A | 3/2000 | Jessup | |
| 6,142,984 A | 11/2000 | Brown | |
| 6,258,075 B1 * | 7/2001 | Taylor et al. | 604/385.18 |
| 6,358,235 B1 * | 3/2002 | Osborn et al. | 604/385.18 |
| 6,554,814 B1 * | 4/2003 | Agyapong et al. | 604/385.18 |

* cited by examiner

PROTECTION TAMPON AND METHOD OF MAKING

CROSS REFERENCE TO RELATED APPLICATIONS

This is a divisional of application Ser. No. 09/695,552 filed on Oct. 24, 2000 now U.S. Pat. No. 6,554,814, which, a continuation in part of application Ser. No. 09/309,467 filed on May 10, 1999, now U.S. Pat. No. 6,258,075.

FIELD OF THE INVENTION

This invention relates to absorbent tampons, applicators for use with such tampons, and methods for making such tampons. More particularly, the invention relates to a tampon having improved leakage protection through improved expansion characteristics and the use of independent protection mechanisms.

BACKGROUND OF THE INVENTION

A wide variety of absorbent catamenial tampons have long been known in the art. Most currently commercially available tampons are made from a tampon pledget which has been compressed into a substantially cylindrical form. Tampon pledgets of a variety of types and constructions have been described in the art. Prior to compression, the pledget may be rolled, spirally wound, folded, or assembled as a rectangular pad of absorbent material. Tampons made from a generally rectangular pledget of absorbent material have been popular and successful in the market.

The absorbent catamenial tampons now in use typically comprise absorbent members which are compressed to a generally cylindrical form about three-eighths to one-half inch (about 1.0 cm to 1.3 cm) in diameter and from about 2 cm to 7 cm in length. In order to provide the desired total absorbency, these absorbent members are usually formed from batts larger in size than the vaginal orifice, which are then compressed to the size (with a corresponding increase in rigidity) indicated above in order to facilitate insertion. As fluid is absorbed, these compressed tampons are expected to re-expand toward their original pre-compressed size, and to eventually become large enough to effectively cover the vaginal cavity against fluid leakage or bypass. While it has been found that these compressed tampons perform their intended function tolerably well, even the best of them do not always re-expand sufficiently, or fast enough, to provide good coverage against leakage.

It has been long recognized that the internal vaginal cavity in its normal collapsed state is of much wider dimension in its transverse plane than in its vertical plane. It is equally well known that the minimum dimension of the vagina is near the introitus while the maximum dimension is near the cervix. It is desirable, therefore, when considering a tampon for catamenial use, to provide a structure which is in its initial state is of a size and/or shape to pass through the vaginal orifice without discomfort, and when once inside the vaginal cavity and beyond the restrictions of the orifice may be expanded, particularly in the lateral direction, to contact substantially all of surface of the vaginal walls from one side to the other in the vaginal cavity to prevent early bypass of the menstrual discharges from the cervix.

The prior art has long recognized various mechanisms by which tampons might fail to deliver superior performance. One such mechanism is often referred to in the art as "bypass" failure. Bypass failure occurs when the menses travels along the length of the vagina without contacting the tampon, i.e. the tampon fails to intercept the flowing menses.

A compressed tampon, to perform well, should re-expand as quickly and fully as possible and should be in a form to provide the best possible anatomical fit. Nevertheless, these needs are not always consistent with the desire to provide a tampon which is sufficiently small and rigid enough to facilitate an easy insertion. Additionally, even after use, the tampon should be as comfortable as possible to remove from the vaginal cavity. Prior art tampons, therefore, attempted to balance these design objectives as best as possible, often having to trade some performance with respect to one objective for improved performance with respect to another.

Typical currently marketed tampons will usually expand in use to a width dimension in a range from about 15 mm to about 26 mm. This may be smaller than the width of the vaginal cavity in its collapsed state. In particular, because the maximum width dimension of the vagina is near the cervix, tampons which are placed within the upper third section of the vaginal canal (which is where tampons are often placed) may not always expand sufficiently, particularly in the width direction, to provide superior coverage. Additionally, typical currently marketed tampons may not even be able to achieve the width dimensions given above when under pressure (such as by the pressure of the vagina during use). Another consideration is the rate and nature of tampon re-expansion which may not always be optimal in currently available tampons.

It is, therefore, desirable to provide a tampon with improved expansion characteristics, particularly in the width dimension. Such a tampon should not introduce new drawbacks, such as a decreased ability to comfortably remove the tampon. Ideally, such a tampon should be able to be manufactured out of materials similar to those currently used for tampons. These materials have the advantages of a proven record of suitability for human use, acceptable cost, and the ability to be manufactured into tampons without undue modifications to current commercially available manufacturing equipment.

It has been found that even the best-designed currently available tampons do not always re-expand as designed in a manner to completely eliminate leakage. Therefore, it is desirable to provide a tampon, which in addition to improved expansion characteristics, is provided with an improved leakage protection mechanism which is independent of tampon re-expansion. Ideally, such tampons would also be provided with an improved applicator to enhance to likelihood that the benefits of the tampon will be achieved by a majority of users.

SUMMARY OF THE INVENTION

This invention relates to catamenial tampons, and more particularly, to tampons having particularly desired expansion characteristics.

A tampon of the present invention which may be sold as a "Regular" absorbent tampon may comprise a mass of absorbent material which has been compressed into a generally cylindrical, self-sustaining form. Subsequent to this compression, the absorbent material preferably has a diameter of less that about 15 mm. The resulting tampon has an absorbent capacity as measured by the standard syngyna test of between about 6 to about 9 grams. The tampon is fluid expanding and preferably has an expanded width upon fluid absorption of at least about 20 mm.

In preferred embodiments the difference between the absorbent material diameter and the tampon expanded width is at least about 6 mm. The difference between the absorbent material diameter and the tampon expanded width may also be at least about 10 mm. Preferably, the mass of absorbent material is subjected to microwave radiation during formation of the tampon.

Another embodiment is a tampon of the present invention which may be sold as a "Super" absorbency tampon. Such a tampon may comprise a mass of absorbent material which has been compressed into a generally cylindrical, self-sustaining form. Subsequent to this compression, the absorbent material preferably has a diameter of less that about 19 mm. The resulting tampon has an absorbent capacity as measured by the standard syngyna test of between about 9 to about 12 grams. The tampon is fluid expanding and preferably has an expanded width upon fluid absorption of at least about 24 mm.

In preferred embodiments the difference between the absorbent material diameter and the tampon expanded width is at least about 8 mm. The difference between the absorbent material diameter and the tampon expanded width may also be at least about 12 mm. Preferably, the mass of absorbent material is subjected to microwave radiation during formation of the finished tampon.

Another embodiment is a tampon of the present invention which may be sold as a "Super Plus" absorbency tampon. Such a tampon may comprise a mass of absorbent material which has been compressed into a generally cylindrical, self-sustaining form. Subsequent to this compression, the absorbent material preferably has a diameter of less that about 22 mm. The resulting tampon has an absorbent capacity as measured by the standard syngyna test of between about 12 to about 15 grams. The tampon is fluid expanding and preferably has an expanded width upon fluid absorption of at least about 27 mm.

In preferred embodiments the difference between the absorbent material diameter and the tampon expanded width is at least about 10 mm. The difference between the absorbent material diameter and the tampon expanded width may also be at least about 15 mm. Preferably, the mass of absorbent material is subjected to microwave radiation during formation of the finished tampon.

Another embodiment is a tampon of the present invention which may be sold as a "Junior" absorbency tampon. Such a tampon may comprise a mass of absorbent material which has been compressed into a generally cylindrical, self-sustaining form. Subsequent to this compression, the absorbent material preferably has a diameter of less that about 15 mm. The resulting tampon has an absorbent capacity as measured by the standard syngyna test of less than about 6 grams. The tampon is fluid expanding and preferably has an expanded width upon fluid absorption of at least about 20 mm. Preferably, the mass of absorbent material is subjected to microwave radiation during formation of the finished tampon.

In an additional embodiment of a tampon of the present invention which may be sold as a "Regular" absorbency tampon, the tampon comprises a mass of absorbent material which has been compressed into a generally cylindrical, self-sustaining form. The resulting tampon has an absorbent capacity as measured by the syngyna test of between about 6 grams and about 9 grams. The tampon demonstrates a rate of expansion as measured by the expansion under pressure test from time zero until two minutes of at least about 1.25 mm/min. In another embodiment the tampon may demonstrate a rate of expansion as measured by the expansion under pressure test from time zero until seven minutes of at least about 0.58 mm/min.

In an additional embodiment of a tampon of the present invention which may be sold as a "Super" absorbency tampon, the tampon comprises a mass of absorbent material which has been compressed into a generally cylindrical, self-sustaining form. The resulting tampon has an absorbent capacity as measured by the syngyna test of between about 9 grams and about 12 grams. The tampon demonstrates a rate of expansion as measured by the expansion under pressure test from time zero until two minutes of at least about 1.6 mm/min. In another embodiment the tampon may demonstrate a rate of expansion as measured by the expansion under pressure test from time zero until seven minutes of at least about 0.82 mm/min.

In an additional embodiment of a tampon of the present invention which may be sold as a "Super Plus" absorbency tampon, the tampon comprises a mass of absorbent material which has been compressed into a generally cylindrical, self-sustaining form. The resulting tampon has an absorbent capacity as measured by the syngyna test of between about 12 grams and about 15 grams. The tampon demonstrates a rate of expansion as measured by the expansion under pressure test from time zero until two minutes of at least about 1.39 mm/min. In another embodiment the tampon may demonstrate a rate of expansion as measured by the expansion under pressure test from time zero until seven minutes of at least about 0.87 mm/min.

An additional embodiment of a tampon of the present invention may comprise a chevron shaped laminar pad. The pad has a width and a length wherein the width is greater than the length. The pad may comprise at least three layers of absorbent material, including an uppermost layer, a lowermost layer, and at least one intermediate layer positioned between said uppermost layer and said lowermost layer. Each of the uppermost layer and the lowermost layer is comprised primarily of rayon, and the at least one intermediate layer is comprised primarily of cotton. The tampon also comprises a withdrawal cord attached to the laminar pad. The withdrawal cord comprises secondary absorbent member joined to the withdrawal cord along at least a portion of its extent. Preferably, the secondary absorbent member may be an integral part of at least a portion of the withdrawal cord.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
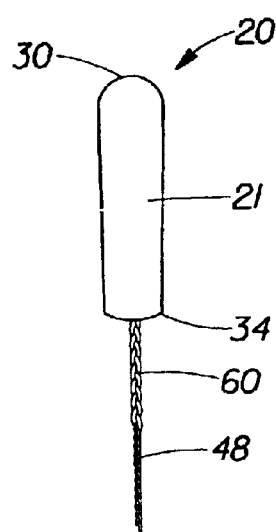
FIG. 1 is a front view of a tampon of the present invention.

The present invention is directed to an absorbent tampon having improved leakage protection though independent protection mechanisms. FIG. 1 shows one embodiment of such an absorbent tampon, tampon 20. The present invention, however, is not limited to a structure having the particular configuration shown in the drawings.

As used herein the term "tampon" refers to any type of absorbent structure which is inserted into the vaginal canal or other body cavities for the absorption of fluid therefrom. Typically, tampons are constructed from an absorbent material which has been compressed in any or all of the width direction, the radial direction, and the axial direction, in order to provide a tampon which is of a size and stability to allow insertion within the vagina or other body cavity. A tampon which has been so compressed is referred to herein as a "self-sustaining" form. That is, the degree of compression applied to the absorbent material of the tampon pledget is sufficient so that in the subsequent absence of external forces, the resulting tampon will tend to retain its general shape and size.

It will be understood by one of skill in the art that this self-sustaining form need not, and preferably does not persist during actual use of the tampon. That is once the tampon is inserted and begins to acquire fluid, the tampon will begin to expand and may lose its self-sustaining form. Preferably, tampons constructed according to the present invention are fluid expanding. As used herein, the term "fluid expanding" means that the tampon which has been compressed to a self sustaining form will expand or uncompress upon contact with fluid such as bodily fluids. Fluid expanding tampons are contrasted to "mechanically expanding" tampons which are tampons which use springs, or some other mechanical supplier of force to expand. An example of such a mechanically expanding tampon is described in U.S. Pat. No. 3,706,311 to Kohx et al.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, and the term "pledget" is intended to include such terms as well.

In general in this specification, the term "tampon" is used to refer to a finished tampon after the compression process referred to above. Generally, the term "pledget" or "tampon pledget" will be used to refer to the absorbent material prior to the compression referred to earlier. It will be recognized by those of skill in the art that in some contexts these terms are interchangeable. The different stages of tampon manufacture are described herein with an eye toward providing the greatest possible clarity. Therefore, the terms used are to assist the reader in best understanding the features of the invention and not to introduce limitations in the terms not consistent with the context in which they are used in this specification.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally are not included within the term "vaginal cavity" as used herein.

The primary absorbent member 21 (sometimes also referred to as the "absorbent core") of the tampon 20 shown in FIG. 1 has an insertion end 30 and a withdrawal end 34. The primary absorbent member 21 may be compressed into a generally cylindrical configuration in the width direction, the radial direction, the axial direction, or in any combination of these directions. Preferably, the greatest compression of the primary absorbent member 21 takes place in the width direction. Head formation of the finished tampon is preferably accomplish by subsequent (and less substantial) compression in the axial direction.

While the primary absorbent member 21 is preferably compressed into a substantially cylindrical configuration, other shapes are also possible. These may include shapes having a cross section which may be described as rectangular, triangular, trapezoidal, semi-circular, or other suitable shapes.

Figure 2:
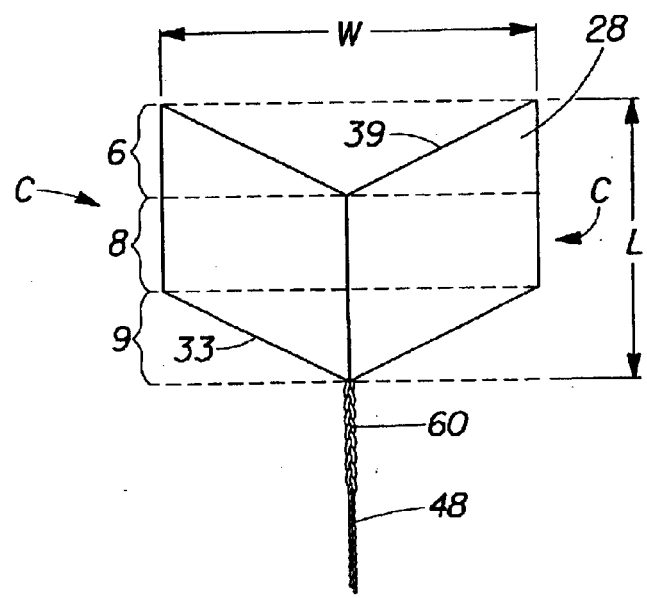
FIG. 2 is a front view of a tampon pledget from which a tampon of the present invention may be made by suitable compression.

The primary absorbent member 21 of the tampon 20 of the present invention may be formed from any suitable tampon pledget, such as tampon pledget 28 shown in FIG. 2. The tampon pledget 28 and, consequently, the finished tampon 20 may also be provided with an optional secondary absorbent material, such as secondary absorbent material 60. This feature will be further described below. The tampon pledget 28 portion of the tampon 20 which will be compressed to form the primary absorbent member 21 may be any suitable shape, size, material, or construction. In the embodiment shown in FIG. 2, pledget 28 is a batt of absorbent material which is a generally "chevron shaped" pad of absorbent material.

Figure 3:
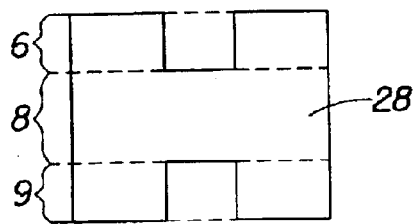
FIG. 3 is a front view of an alternative shape for a tampon pledget.
Figure 4:
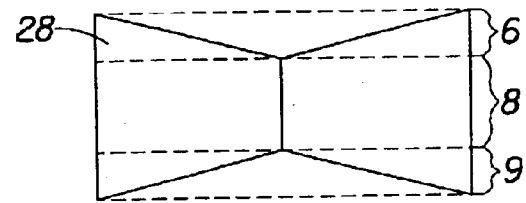
FIG. 4 is a front view of another alternative shape for a tampon pledget.

While the pledget 28 shown in FIG. 2 is generally chevron shaped, other shapes such as trapezoidal, triangular, semicircular, and rectangular shaped are also acceptable. Preferably, the pledget 28 may be divided into three regions, top region 6, middle region 8, and bottom region 9. In preferred embodiments, the pledget 28 is shaped such that the middle region 8 is a region having more absorbent material than the top region 6 or the bottom region 9. As shown in FIG. 2, the chevron shape of pledget 28 provides such a variation in absorbent material amounts. Other shapes which also tend to produce this variation are also possible. For example, the pledget may be generally "H" shaped, such as shown in FIG. 3. A "bow tie" shape such as is shown in FIG. 4 is also suitable. While a chevron shaped pledget 28 is suitable, the edges of the chevron may be somewhat "rounded off" in order to facilitate high speed manufacturing operations. As an alternative to the shapes of pledgets described above, a tampon pledget of the present invention may have a uniform shape such as a rectangular shape, but vary in absorbent material density or thickness along the axial extent of the pledget.

Figure 5:
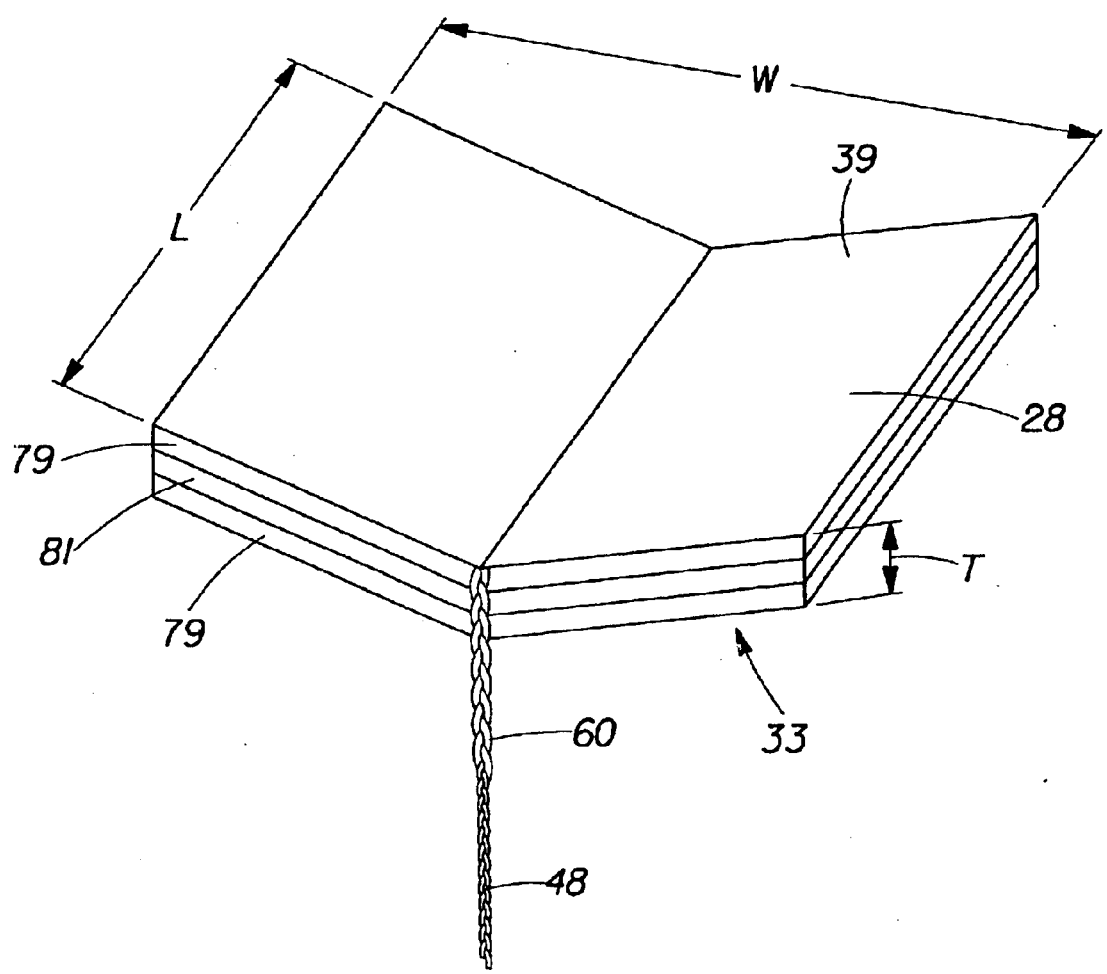
FIG. 5 is a perspective view of the tampon pledget shown in FIG. 2 which shows the layers of such pledget.

In preferred embodiments, the pledget 28 may be a laminar structure comprised of integral or discrete layers. As is shown more clearly in FIG. 5, the pledget 28 may comprise outer layers 79 and at least one intermediate layer 81 positioned between the outer layers 79. In other embodiments, the pad need not have a layered structure at all. The pledget 28 may comprise a folded structure, may be rolled, may comprise a "petal" structure or any other of the structures which are known in the art with respect to tampon pledgets.

The pledget 28, and consequently, the resulting primary absorbent member 21 of the tampon 20 may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these.

Preferred absorbent materials comprise cotton, rayon (including tri-lobal and conventional rayon fibers, and needle punched rayon), folded tissues, woven materials, nonwoven webs, synthetic and/or natural fibers. The tampon 20 and any component thereof may comprise a single material or a combination of materials. Additionally, superabsorbent materials, such as superabsorbent polymers or absorbent gelling materials may be incorporated into the tampon 20.

In the preferred embodiment shown in FIGS. 1–2, the pledget 28 and resulting primary absorbent member 21 is formed of a soft absorbent material such as rayon, cotton (including either long fiber cotton or cotton linters) or other suitable natural or synthetic fibers or sheeting. The materials for the tampon 20 can be formed into a fabric, web, or batt that is suitable for use in the pledget 28 by any suitable process such as airlaying, carding, wetlaying, hydroentangling, or other known techniques.

In one non-limiting preferred embodiment, the tampon pledget 28 and resulting primary absorbent member 21 comprise rayon, cotton, or combinations of both materials. The rayon used in the tampon pledget 28 may be any suitable type typically used in disposable absorbent articles intended for in vivo use. Such acceptable types of rayon include GALAXY Rayon (a tri-lobed rayon structure) available as 6140 Rayon from Acordis Fibers Ltd., of Hollywall, England. SARILLE L rayon (a round fiber rayon), also available from Acordis Fibers Ltd. is also suitable. Any suitable cotton material may be used in the tampon pledget 28. Suitable cotton material includes, long fiber cotton, short fiber cotton, cotton linters, T-fiber cotton, card strips, and comber cotton. Preferably, the cotton layers should be a scoured & bleached cotton absorbent with a glycerin finish, a leomin finish, or other suitable finish.

The absorbent material of the pledget 28 may be surrounded with a liquid permeable overwrap material, if desired. Such overwrap materials may comprise rayon, cotton, bicomponent fibers, or other suitable natural or synthetic fibers known in the art. Rayon, polyethylene, polypropylene and blends of these are particularly suited for use as overwrap material. If the pledget 28 of the present invention is layered, the layers may comprise different materials. For example, in the embodiment shown in FIG. 5 the outer layers 79, may comprise primarily rayon, while the intermediate layer 81 or layers may comprise primarily cotton. Optionally, the entire pledget 28 may comprise a uniform or non-uniform blend of materials throughout. In preferred layered embodiments, each of the layers may comprise essentially 100% of the same material, such as outer layers 79 of 100% rayon and an intermediate layer 81 of 100% cotton.

Tampons of the present invention offer several advantages over tampons which are known in the art. These advantages fall into several categories, and the benefits of each will be discussed separately. It is not necessary that a tampon of the present invention incorporate all of the advantages which are described in this specification. Any combination of the new and useful features which are described and claimed may be included in any desired combination. In the most preferred embodiments, all of the novel features described are utilized in combination in order to achieve the maximum benefit of the features of the present invention. Nevertheless, a tampon may be made according to the present invention which incorporates some, but not all of the features described in this specification. Such a tampon will still offer improved performance over tampons currently available even though further benefits could be attained by incorporation of remaining preferred features.

It will be appreciated by those of skill in the art that the tampons of the present invention are in many respects similar to those which are currently available. Nevertheless, there are important and unapparent differences between tampons of the present invention and current tampons. These differences lead to surprising and significant differences in tampon performance. Additionally, the similarity to current tampons is also an advantage of the present invention. For example, it is preferred that tampons of the present invention be made out of materials which are currently used for catamenial tampons such as rayon and cotton. These materials have a proven record of suitability for use in the human body. It is also desirable that tampons of the present invention be made in the absorbency ranges which are currently required by the United States Food and Drug Administration and corresponding agencies of many other governments which regulate tampon absorbency. In fact, one of the benefits of the present invention is that it provides tampons having improved protection characteristics without a corresponding increase in absorbency. Tampons of the present invention may be manufactured in a manner which is similar to that currently used for present tampons. While some equipment modification is typically required to take advantage of all features of the present invention, it is not necessary to start with a completely new manufacturing plant, for example. This feature is another advantage of some of the similarities between tampons of the present invention and currently available tampons.

While describing the features of the present invention, this specification will focus on the differences (and corresponding benefits which come from these) between tampons of the present invention and prior art tampons. One of skill in the art will appreciate from this description how to make and use tampons incorporating the various features of the present invention although not every conventional feature is described in undue detail.

In order to better understand the present invention, a detailed description of several preferred embodiments is given. This description is intended to be by way of example, and not to limit the invention to these preferred embodiments. FIGS. 1–2, respectively, generally show one preferred embodiment of the primary absorbent member 21 of a tampon (such as tampon 20) made from a tampon pledget 28 of the present invention. The pledget 28, has a width W and a length L, both of which are shown in FIG. 2. The thickness of the pledget is perpendicular to both the width W and the length L, and is the dimension represented as thickness T in FIG. 5. Preferably, each of the width W, and length L, exceed the thickness T resulting in a pledget 28 which is generally in the shape of "flat sewn pad" prior to compression.

As mentioned previously, it is desired to provide tampons of the present invention which fall within the absorbency ranges proscribed by tampon governmental regulations in the United States and elsewhere. Therefore, a "Super Plus" absorbency tampon should have a total absorbency as measured by the industry standard Syngyna test of 12–15 grams. A "Super" absorbency tampon should have a total absorbency as measured by the Syngyna test of 9–12 grams. A "Regular" absorbency tampon should have a Syngyna absorbency of 6–9 grams. A "Junior" absorbency tampon should have a Syngyna absorbency of less than 6 grams. Providing a tampon which properly falls within these absorbency ranges requires that the total amount and type of absorbent material be controlled. Given limits on the total absorbency for each range, the challenge is to design a tampon which can be easily inserted and also take full advantage of the limited amount of absorbent material which may be used.

A tampon of the present invention preferably demonstrates improved expansion characteristics as compared to prior art tampons. These improved expansion characteristics may be described and measured in several different ways. For example, a tampon of the present invention preferably expands to a final width dimension which is greater than that seen by prior art tampons of similar absorbency. Preferably, this increased widthwise expansion is also seen when the tampon is under pressure such as would be experienced by the tampon during actual use in the body. Ideally, the tampon of the present invention expands in the width dimension at a rate exceeding that demonstrated by prior art devices. Preferably, the widthwise expansion of the tampon of the present invention is essentially uniform throughout its length rather than being concentrated toward the top portion of the device.

Each of these improved expansion characteristics and their significance will be explained in turn. As noted The challenge which is met by the present invention is to provide a tampon which is initially not significantly wider than current tampons, but which can expand in the width dimension to a greater degree than these tampons upon fluid acquisition. These objectives should be accomplished while simultaneously not increasing the total absorbent capacity of the device. The improvement thus may be thought of as an improvement in the efficient use of absorbent material rather than a simple increase in total size and/or mass to achieve an improved width upon expansion.

Table 1, below presents the results of widthwise expansion testing (using the expanded width test described in the TEST METHODS section below) performed on tampons of the present invention and a variety of prior art tampons. The table shows an initial or "dry" diameter for each tampon. This is the diameter of the compressed tampon before any fluid has been acquired. Table 1 also shows the expanded width. Briefly, this expanded width was determined by placing each tampon into the standard FDA proscribed Syngyna apparatus and measuring the width (or largest linear dimension) of the tampon at its widest point upon the tampon reaching its leakpoint and being removed from the test apparatus. The various tampons shown in the table are shown in multiple absorbencies.

TABLE 1

|  | Super Plus | | Super | | Regular | | Junior | |
| --- | --- | --- | --- | --- | --- | --- | --- | --- |
| Product | dry diam. | exp. width | dry diam. | exp. width | dry diam. | exp. width | dry diam. | exp. width |
| A | 15 mm | 33 mm | 14 mm | 29 mm | 13 mm | 25 mm | 12 mm | 23 mm |
| B | 16 mm | 26 mm | 15 mm | 23 mm | 14 mm | 18 mm | | |
| C | 15 mm | 24 mm | 14 mm | 21 mm | 13 mm | 18 mm | | |
| D | 14 mm | 22 mm | 14 mm | 19 mm | 13 mm | 15 mm | | |
| E | | | 15 mm | 22 mm | 13 mm | 19 mm | | |

A = Chevron shaped pledget tampon according to present invention
B = PLAYTEX GENTLE GLIDE tampon
C = OB Digital Tampon
D = TAMPAX SATIN tampon
E = Unicharm CHARMSOFT Tampon previously, the vaginal canal is known to be wider in the transverse plane than it is in the vertical plane. This would indicate that greater widthwise expansion of an inserted tampon would tend to reduce the potential for "bypass" leakage in the early stages of tampon use. In other words, by expanding quickly in the width dimension, the absorbent surface of the tampon is more likely to be available to contact fluid across the full width of the vaginal canal.

One manner in which the width of the tampon in the body can be increased is to use a significantly wider or larger quantity of absorbent material from which to construct the tampon pledget. This approach, however, may be unacceptable for several reasons. Using too large a quantity of absorbent material, or a mass of material which is too wide may not yield a tampon which can be compressed to an acceptable initial size. Indeed, early tampons (e.g. those shown in the art in about the 1960's and 1970's) tended to have desirable widthwise expansion. Unfortunately, these tampons were significantly more bulky when compressed than tampons of the present invention. This initial bulkiness results in insert comfort issues and may also contribute to removal comfort issues. Additionally, the use of additional material is not an acceptable approach to achieve improved widthwise expansion due to the desire not to increase total absorbent capacity of the tampon device.

It is readily appreciated that the tampons of the present invention for each absorbency have an initial diameter which is similar to those of current tampons. The tampons of the present invention, however, demonstrate significantly greater expansion in the width dimension for each absorbency than other tampons. One reason for this is that the current tampons expand in several directions while the tampons of the present invention are designed to focus their expansion primarily one direction (i.e. the width direction) to achieve maximum side to side coverage. This results in a more efficient use of the (limited) amount of absorbent material available for fluid acquisition.

Tampons according to the present invention may also be contrasted with absorbencies greater than Super Plus. In some regions these tampons are used by some consumers. Preferably, such a high absorbency tampon of the present invention has an initial width of no greater than 19 mm. Preferably, the expanded width of such a high absorbency tampon is at least about 30 mm. Such a tampon may generally be constructed according the guidance given herein with respect to the Super Plus absorbency range, but with a corresponding in absorbent material amount.

Without wishing to be bound by theory, several factors in the design of the tampon of the present invention are believed to lead to the improved widthwise expansion described above. It should be noted, that as used in this embodiment, the term "improved widthwise expansion" refers to a tampon made according to the present invention which is characterized by a maximum initial diameter, a minimum expanded width (upon fluid acquisition in the Syngyna test), and an absorbency within a particular range prescribed by the FDA (the regulated absorbency ranges having been previously described above). The tampon pledget 28 of the present invention is typically made shorter in the length dimension L and wider in the width dimension W than many currently available tampons. For example, for a tampon in the "Super Plus" or "Super" absorbency ranges (i.e. 12–15 grams, and 9–12 grams, respectively), length and width dimensions of about 46 mm by about 70 mm have been found to work well.

Simply making the tampon pledget 28 wide, however, is not sufficient to achieve the improved widthwise expansion demonstrated by the tampon of the present invention. It has been found during development of the present invention that if the length dimension L of the tampon pledget 28 is reduced too greatly, the tampon will have insufficient stability upon compression and will not be amenable to reliable insertion. Therefore, even as the width of the pledget 28 is increased, it is important not to make the length of the pledget too short such that effective compression is jeopardized.

These considerations can be problematic as it will be noted that the total amount of absorbent material must be controlled in order to keep the total absorbency within the target range. The chevron shape of the pledget shown in FIG. 2, is one manner in which both the width W and the Length L of the pledget 28 may be maximized without creating a pledget 28 having an unacceptably large total volume of absorbent material. The alternative pledget shapes shown in FIGS. 3 and 4 also allow for both increased total width and length of the pledget without exceeding the total desired capacity of the resulting tampon. Another benefit of chevron shaped pledget shown in FIG. 2 and the alternative shapes shown in FIGS. 3–4 is that these shapes result in a greater amount of absorbent material across the full width W of the pledget 28 in the middle region 8. This results in an absorbent core 21 in which the greatest energy of compression is stored in the middle region 8 of the absorbent core 21. Consequently, the middle region 8 tends to release the greatest amount of expansion energy and drives the lateral expansion of the entire tampon. As noted, this is in contrast to prior tampon devices in which lateral expansion may tend to be focused only at the top of the device rather than across its full length. While the shapes shown in FIGS. 2–4 are desirable, the improved expansion characteristics described may also be achieved by imparting a high basis weight per unit length of absorbent material into the pledget 28. In other words, a high amount and/or a high concentration of absorbent material, particularly in the middle region 8 helps to increase the compression energy, and consequently the expansion energy of the finished tampon 20. The basis weight of the absorbent material may be greater in the middle 8 than in the top region 6 or bottom region 9 of the pledget 28.

The chevron shape shown in FIG. 2 is particularly preferred because the top portion 39 is notched in a manner which facilitates head formation of the finished tampon. Correspondingly, the oppositely inflected bottom portion 33 of the chevron is shaped in a manner which facilitates comfortable removal by helping to gradual spread the vaginal introitus as the tampon is removed following use.

In addition to selection of the size and shape of the pledget 28, attention should be paid to the manner in which the pledget 28 is conditioned and compressed. It has been found during development of the present invention that improved widthwise expansion of the tampon is enhanced when the pledget is compressed primarily in the widthwise direction. This direction is indicated in FIG. 2 with arrows C showing this direction of compression following compression in the width direction C, the pledget may be axially compressed against a head forming die to achieve head formation. Preferably, however, any axial compression is minimized in order to allow for maximum re-expansion of the tampon in the widthwise direction rather than the axial direction.

Prior art tampons tend to be compressed in a manner which does not lead to the widthwise expansion efficiency shown by tampons of the present invention. For example, many tampons are spirally wound and then radially compressed (i.e. compressed from the sides essentially uniformly in all directions). Such a tampon has essentially equal amounts of energy imparted in all directions during compression. Therefore, during re-expansion this energy will be released in a variety of directions about the radial axis of the tampon. This may not be optimal as the vaginal canal is known to be greater in its side to side dimension than in its width. A tampon which expands in several directions, will tend to be too narrow with respect to side to side coverage and will simply tend to stretch the vaginal cavity in the other directions in which it expands. Therefore, the tampon of the present invention maximizes coverage of the vaginal interior by focusing re-expansion in the width dimension where it is expected to be more effective. Other prior art tampons are compressed most significantly in the axial direction rather than the radial direction. This results in a tampon which tends to re-expand primarily in this axial direction, thereby reducing the ability of the tampon to recover its initial width fully.

In the preferred embodiment of the present invention shown in FIGS. 1–2 (and described in Table 1.) the Super and Super Plus absorbency pledget 28 may be about 70 mm in width W and 46 mm in length L. The Regular absorbency pledget 28 may be about 50 mm in width W and 40 mm in length L. The Junior absorbency pledget may be about 40 mm in width W and 30 mm in length L. These dimensions are the initial dimensions of the pledget 28 prior to compression. Preferred material compositions for tampons of the present invention are GALAXY rayon described above with cotton fibers as described above. A super plus absorbency tampon of the present invention may be made from a pledget 28 comprising about 67% rayon and about 33% cotton fibers. A super absorbency or regular absorbency tampon of the present invention may be made from a pledget 28 comprising about 50% cotton and about 50% rayon fibers. A junior absorbency tampon may be made from a pledget 28 comprising about 67% cotton and about 33% rayon fibers.

Conventional compression temperatures and pressures using standard equipment such as a tampon compressor machine available from Hauni Machines, Richmond, Va., are suitable. Preferably, the direction of compression is primarily in the lateral direction as described above. In particularly preferred embodiments, the pledget 28 is subject to microwave conditioning during tampon formation. Without wishing to be bound by theory, this step is believed to heat water within the fibers of the pledget. This allows greater flexibility in the compression step. For example, if microwave conditioning is used, lower temperatures (such as room temperature or slightly elevated temperatures) during the compression step are sufficient for formation of the final tampon 20. It will be recognized by those of skill in the art that compression to a self sustaining form requires imparting both heat and pressure to the tampon pledget 28. Such heat and pressure causes the fibers to "set" and achieve this self-sustaining form subject to fluid expansion. Typically, the heat and pressure are provided simultaneously with a heated compression die. This may result in several drawbacks, however. The outer portion of the pledget which contact the compression die may tend to become scorched due to the localized heat. Additionally, the heat imparted by the die may not penetrate into the tampon in a uniform manner. The microwave conditioning overcomes these drawbacks by allowing the pressure to be imparted with a much cooler (for example, room temperature) die. The heat required is imparted by the microwaves which penetrate the tampon more uniformly and which do not tend to scorch the fibers of the tampon. This microwave conditioning is also believed to contribute the improved expansion properties associated with the present invention.

Preferably, the tampon pledget 28 of the present invention is subject to conditioning a microwave source for about 18 seconds +/- about 5 seconds. Junior absorbency tampons may be subject to this microwave source at a power level of about 3 kW. Regular absorbency tampons are preferably subject to microwaves at a power level of about 5 kW. Super absorbency tampons are preferably subject to microwaves at a power level of about 7 kW. Super absorbency tampons are preferably subject to microwaves at a power level of about 8.5 kW.

As previously noted, in addition to an increased final widthwise expansion, tampons of the present invention preferably also demonstrate an increased widthwise expansion under pressure than tampons available in the art. The ability to expand in the width dimension under pressure is an indication that the tampon will perform well (and provide superior coverage of the vaginal canal) during conditions which approximate those of actual use (i.e. when subjected to the pressure exerted on the tampon by the vaginal canal itself). The preferred design characteristics of a tampon of the present invention described above with respect to final widthwise expansion also are suitable design considerations to make a tampon according to the present invention which results in increase widthwise expansion under pressure.

Table 2, below presents the results of expansion under pressure testing performed on tampons of the present invention and a variety of prior art tampons. The method used for this test is a modification of the standard Syngyna test. This method is more fully described in the TEST METHODS section below and is referred to as the "expansion under pressure test." The table shows an initial or "dry" diameter for each tampon as in Table 1. Table 2 also shows the expanded width under pressure at leakage for each tampon.

TABLE 2

| Product | Super Plus | | Super | | Regular | | Junior | |
| --- | --- | --- | --- | --- | --- | --- | --- | --- |
| | dry diam. | width under p. | dry diam. | width under p. | dry diam. | width under p. | dry diam. | width under p. |
| A | 15 mm | 25 mm | 14 mm | 24 mm | 13 mm | 22 mm | 12 mm | 19 mm |
| B | 16 mm | 23 mm | 15 mm | 21 mm | 14 mm | 18 mm | | |
| C | 15 mm | 22 mm | 14 mm | 20 mm | 13 mm | 17 mm | | |
| D | 14 mm | 22 mm | 14 mm | | 13 mm | | | |
| E | | | 15 mm | 18 mm | 13 mm | 14 mm | | |

A = Chevron shaped pledget tampon according to present invention
B = PLAYTEX GENTLE GLIDE tampon
C = OB Digital Tampon
D = TAMPAX SATN tampon
E = Unicharm CHARMSOFT Tampon It is seen in Table 2. that the tampons of the present invention retain their widthwise performance advantage even when loaded with fluid under pressure.

Another advantage in expansion characteristics demonstrated by tampons of the present invention is the rate of expansion. That is, in addition to achieving superior side to side coverage, the tampons of the present invention also expand more quickly upon first fluid contact. This allows them to be more quickly available to contact and absorb flow in the earliest stages of wear. As described in the TEST METHODS section below, the expansion under pressure test may also be used to determine the rate of expansion as the flow rate of fluid deposited is controlled during the test. Table 3, below, provides the expansion rate of tampons of the present invention compared to prior art tampons in mm/min as measured by the expansion under pressure test.

TABLE 3

| Product | Regular | Super | Super Plus |
| --- | --- | --- | --- |
| A at 2 min. | 1.83 mm/min. | 2.1 mm/min. | 1.83 mm/min. |
| A at 3 min. | 1.64 mm/min. | 1.9 mm/min. | 1.75 mm/min. |
| A at 7 min. | 1.12 mm/min. | 1.2 mm/min. | 1.25 mm/min. |
| B at 2 min. | 0.42 mm/min. | 0.73 mm/min. | 1.38 mm/min. |
| B at 3 min. | 0.65 mm/min. | 0.92 mm/min. | 1.22 mm/min. |
| B at 7 min. | 0.5 mm/min. | 0.66 mm/min. | 0.86 mm/min. |
| C at 2 min. | 1.24 mm/min. | 1.5 mm/min. | 1.13 mm/min. |
| C at 3 min. | 0.91 mm/min. | 1.3 mm/min. | 1.1 mm/min. |
| C at 7 min. | 0.57 mm/min. | 0.81 mm/min. | 0.72 mm/min. |
| D at 2 min. | 0.92 mm/min. | 0.38 mm/min. | |
| D at 3 min. | 0.73 mm/min. | 0.51 mm/min. | |
| D at 7 min. | 0.45 | 0.38 | |

A = Chevron shaped pledget tampon according to present invention
B = OB Digital Tampon
C = PLAYTEX GENTLE GLIDE tampon
D = Unicharm CHARMSOFT Tampon As shown in Table 3. the rate of expansion of tampons of the present invention is significantly greater than prior art tampons. For example, a regular absorbency tampon of the present invention expands at a rate which is about 50%, about 80%, and about 96% faster than the next fastest prior art tampon from time zero to time=2 minutes, 3 minutes, and 7 minutes, respectively.

Another significant expansion characteristic of the present invention is the substantial uniformity of widthwise expansion along the axial extent of the tampon. U.S. Pat. No. 6,039,716 issued to Jessup et al., for example, describes a tampon which purports to achieve improved widthwise expansion (although not to the degree achieved by the tampon of the present invention). The tampon device described in the Jessup et al. patent, however, experiences most of its expansion near the insertion end of the device and shows little to no expansion near the withdrawal end. By contrast, the tampon of the present invention preferably expands to nearly the same width along the entire length of the tampon. Preferably, the width of the expanded tampon is uniform within about 5 mm along its entire length L after it has expanded upon fluid loading. This characteristic is significant because if expansion is concentrated only at the top of the tampon, significant by-pass flow may result. For example, if fluid bypasses the top of the tampon and first contacts the tampon in at a location in its middle region 8, a tampon which expands primarily in its top region will not tend to cover the vaginal canal at the location where bypass flow is occurring.

As discussed above, a tampon of the present invention having a primary absorbent member 21 constructed in accordance with the guidance described and claimed herein offers meaningful improvements over tampons available in the prior art. It has also been found that these benefits can be even further enhanced by combining these improved expansion characteristics with other tampon features which use independent protection mechanisms in combination. For example, any of the embodiments of the primary absorbent member 21 made from any of the embodiments of a tampon pledget 28 of the present invention may optionally be provided with a secondary absorbent member or material such as secondary absorbent member 60 shown in FIGS. 1–2.

Commonly assigned and co-pending U.S. application Ser. No. 09/309,467, filed on May 10, 1999 in the name of Taylor et al. describes tampons having a variety of secondary absorbent members in great detail. Any of the configurations given in this application are suitable for use as an optional secondary absorbent member in the present invention. In particular, a "fancy yarn" type of combination withdrawal cord 48 and secondary absorbent member 60 is suitable and one potential embodiment for a secondary absorbent member for use with the present invention. As shown in FIGS. 1–2, this fancy yarn may comprise a generally braided (or twisted) withdrawal cord. A conventional type of withdrawal cord (in terms of thickness, material composition, etc.) may be periodically braided with a thicker slub of absorbent fibrous material to form a "fancy yarn" type secondary absorbent member 60. In such an embodiment, the portion of the cord which will act as the withdrawal cord and not the secondary absorbent member may be treated to make the same non-absorbent or even hydrophobic.

As discussed in the previously referenced Taylor et al. application, it has been found that there are several potential mechanisms beyond simple bypass flow which may contribute to tampon leakage. Without wishing to be bound by theory, some of these mechanisms may be explained by the following observations. It has been found that many current tampons show stains on the withdrawal cord associated with incidents of tampon leakage. Therefore, the withdrawal cord of many current tampons may be offering an "escape" route for menses present at the base of the vagina.

During a tampon change, some residual menses may be left near the introitus of the vagina. This may be fluid which was previously absorbed, but which subsequently "squeezed out" of the tampon as it was withdrawn through the sphincter of the vagina. Such residual fluid, particularly if located near the introitus (i.e. in the lower vaginal vault) may not be effectively absorbed by the replacement tampon. This is particularly true of many current tampons which are typically inserted somewhat more deeply within the vaginal canal. These mechanisms, as well as bypass described above, and other leakage mechanisms are addressed by providing the tampon 20 with the optional secondary absorbent member 60.

Providing a tampon of the present invention with any of the varieties of secondary absorbent members 60 described in the previously referenced Taylor et al. application will result in the benefits associated with the secondary absorbent material as described in that application. Additionally, it has been found that the combination of protection benefits associated with the secondary absorbent member 60 and the improved expansion characteristics of the present invention work particularly well in combination to achieve previously unexpected levels of protection.

Again, without wishing to be bound by theory, it is believed that the secondary absorbent material 60 and the improved expansion characteristics of the present tampon operate independently of each other and act in combination to complement the advantages of each. For example, prior to the first contact with fluid by the primary absorbent core 21, the secondary member is available to absorbent fluid and preferably also direct it toward the primary core 21. When this feature is combined with the significant and rapid expansion of the primary core 21, the chance that fluid will escape past the tampon 20 without being intercepted by at least one of the primary core 21 or secondary absorbent member 60 is substantially reduced.

The tampon 20 of the present invention may be inserted digitally or through the use of an applicator. Any of the currently available tampon applicators may also be used for insertion of the tampon of the present invention. Such applicators of typically a "tube and plunger" type arrangement and may be plastic, paper, or other suitable material. Additionally, a "compact" type applicator is also suitable.

Preferably, a partially directionally oriented applicator may be used for insertion of the tampon of the present invention. An example of a suitable applicator is shown and described in U.S. Des. Pat. No. 415,565 issued on Oct. 19, 1999 to Harry Hayes et al. An advantage of an applicator such as that shown in the Hayes patent is that is has directionality. For example, many tampon applicators have a generally cylindrical configuration and are therefore may be held in any orientation by the user. An applicator such as that described in the Hayes patent has flattened grip surfaces which dictate the orientation in which a user will hold the inserter. Therefore, in preferred embodiments, the tampon 20 may be oriented such that the primary direction of expansion will be side to side (with respect to the user's body). This can be reliably achieved with a directionally oriented applicator.

Test Methods

Expanded Width Test

This test is performed according the standard FDA syngyna test using standard syngyna equipment. The standard syngyna test is performed on a tampon to be tested. When the tampon reaches its leakpoint, the tampon is removed from the syngyna apparatus. A suitable rule or scale (preferably an electronic scale using a digital camera or similar device) is used to measure the largest dimension of the tampon in a direction perpendicular to the length dimension. The largest dimension (which is defined as "width" for purposes of this test) is measured at the widest point of the tampon. If the expanded tampon is generally cylindrical, the widest diameter is taken as the width.

Expansion Under Pressure Test

This test is a modification of the standard syngyna test. The test may be used to determine the widthwise expansion under pressure of tampons made according to the present invention. Additionally, this test produces measurements of tampon width as a function of time from the start of the test. These measurements may be used to calculate a widthwise expansion rate by dividing the width at a given time interval minus the width at time zero by the total time elapsed in such time interval.

Figure 6:
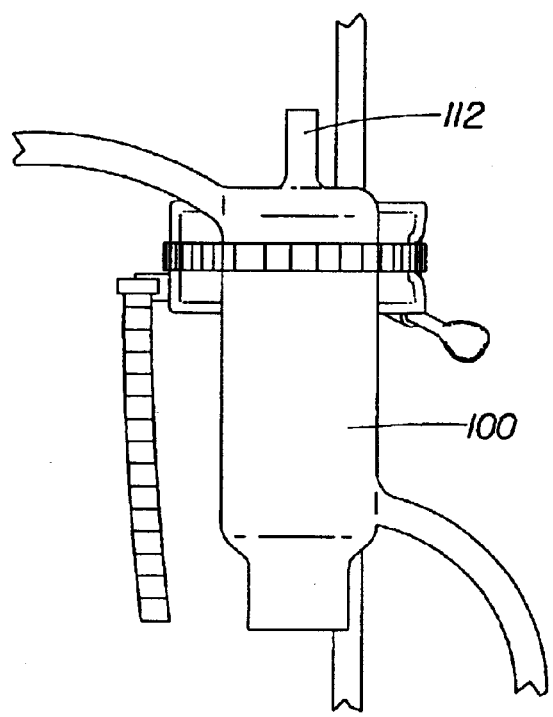
FIG. 6 is a front view of the syngyna test apparatus used to conduct the syngyna test, the expanded width test, and the widthwise expansion test described in this specification.
Figure 7:
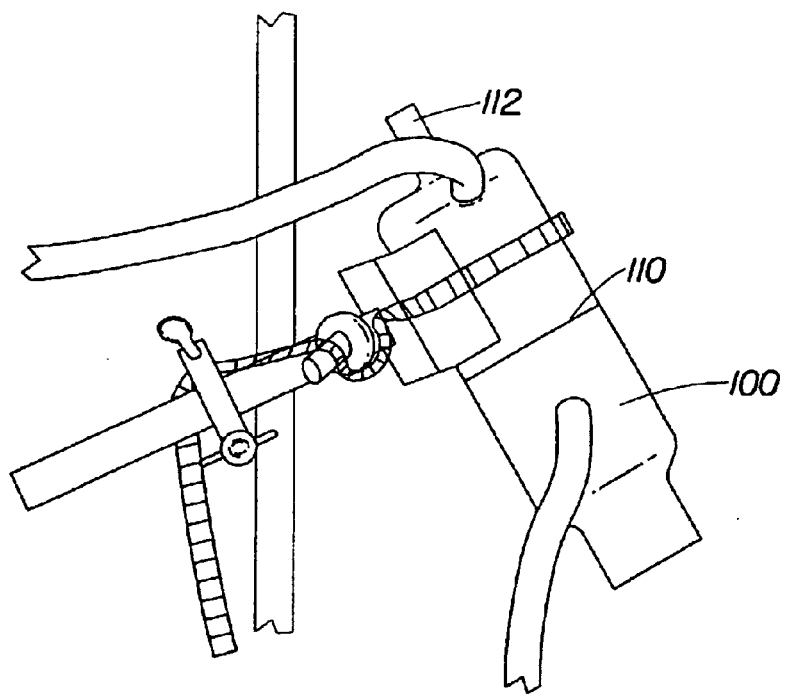
FIG. 7 is a side view of the apparatus shown in FIG. 6.

Procedures:
1. Use the following equipment.
    a) Ring stand
    b) Clamp, chain; VWR #21573-275
    c) Calibrated syngyna chamber
    d) Clamp, swivel; 21572-603 VWR
    e) Compressed air station with PSI gauge
    f) 40 inches of 6409-13 tubing (size 13; Tygon)
    g) Steel cylinder standards
    h) condoms, Calatex
    i) Steel cannula, peristaltic pump head and drive motor
    j) Beakers
    k) Traceable timer
    l) Rule
    m) 06429-18 tubing for air pressurizing of chamber ⅜" I.D.
    n) Tubing clamp
    o) Digital camera
    p) Leveling protractor
    q) KLC 9-25-00 not needed 2. Set up equipment as pictured in FIG. 6.
3. Setup tripod and camera in front of syngyna chamber 100. Place camera as close to the chamber as possible while still being able to see the entire chamber in the view finder.
4. Adjust angle of chamber to 30° from upright (60° on protractor) as shown in FIG. 7.
5. Adjust angle of camera to 30° so that it is parallel to the chamber. Looking through view-finder, the calibration line 110 should be even and solid.
6. Assemble pump head and motor; insert tubing; insert cannula into tubing.
7. Insert a condom into the syngyna chamber, cut off tip and secure top and bottom around ends of chamber with rubberbands. (Same procedure as in syngyna method). Place small rule inside chamber in front of condom, then secure bottom of condom around opening of chamber.
8. Turn on pump motor and dispense test fluid (Sheep's blood, definbrinated) for a set period of time into a tared beaker. Weigh beaker and determine flow rate. Target is 1 gram per minute.
9. Insert tampon into chamber, centering it using calibration line 110.
10. Close clamp on air tube and turn on air pressure. Adjust to 0.25 psi.
11. Insert cannula into top of chamber 112. Be sure it touches top of tampon.
12. Check angle of chamber again. Check set-up by looking through viewfinder of camera. Be sure everything is straight and level. Be sure timer is visible in frame.
13. Take a picture of dry tampon in chamber. This will be time=0.
14. Start pump and timer simultaneously.
15. Take a picture of tampon each minute until it leaks.
16. At leak point, release pressure in chamber and remove tampon.
17. Download images to computer.
18. Using ScionImage analysis software, open each image and measure at least one or two rules. That is, use the measurement line to draw a line over a certain number of millimeters on the rule in an image. Then select "Analyze" on menu bar, then "set scale". Type in number of millimeters measured in image. The software will then set a pixels per-millimeter scale.
19. Using the same measurement line tool, measure the tampon in the image. Measure the widest portion of the tampon as well as the width at the top and bottom of the tampon. For purposes of this instruction, the "top" of the tampon to the widest part above the calibration line on the chamber. The "bottom" is approximate—by 7 mm from the bottom most edge of the tampon.
20. Record measurements.
21. Verification measurements can be made on known standards such as cylinders.
22. Special notes: Periodically check angle of camera and be sure set-up is not disturbed. Check angle of chamber after insertion of each tampon. While it is not necessary to set scale for each image, it is recommended to do so frequently. It is recommended to check scale by measuring rule in image at least every two images.

This concludes the test.

Standard Syngyna Test

An unlubricated condom, with tensile strength between 17 Mega Pascals and 30 Mega Pascals is attached to the large end of a glass chamber with a rubber band and pushed through the small end of the chamber using a smooth, finished rod. The condom is pulled through until all slack is removed. The tip of the condom is cut off and the remaining end of the condom is stretched over the end of the tube and secured with a rubber band. A preweighed (to the nearest 0.01 gram) tampon is placed within the condom membrane so that the center of gravity of the tampon is at the center of the camber. An infusion needle (14 guage) is inserted through the septum created by the condom tip until it contacts the end of the tampon. The outer chamber is filled with water pumped from a temperature-controlled waterbath to maintain the average temperature at 27±1° C. The water returns to the waterbath. Syngyna fluid (10 grams sodium chloride, 0.5 gram Certified Reagent Acid Fushsin, 1,000 milliliters distilled water) is then pumped through the infusion needle at a rate of 50 milliliters per hour. The test shall be terminated when the tampon is saturated and the first drop of fluid exits the apparatus. (The test result shall be discarded if fluid is detected in the folds of the condom before the tampon is saturated). The water is then drained and the tampon is removed and immediately weighed to the nearest 0.01 gram. The absorbency of the tampon is determined by subtracting its dry weight from this value. The condom shall be replaced after 10 tests or at the end of the day during which the condom is used in testing, whichever occurs first.

The disclosures of all patents, patent applications (and any patents which issue thereon) referred to in this specification (including those listed in the Cross Reference to Related Applications Section) are hereby incorporated by reference as if fully set forth herein. While particular embodiments of the present invention have been illustrated and described, it would be obvious to those skilled in the art that various other changes and modifications can be made without departing from the spirit and scope of the invention.

It is expressly not admitted, however, that any of the documents incorporated by reference herein teach or disclose the present invention. It is also expressly not admitted that any of the commercially available materials or products described herein teach or disclose the present invention.

What is claimed is:

1. An absorbent tampon comprising:
a mass of absorbent material which has been compressed into a generally cylindrical, self-sustaining form, wherein subsequent to said compression said generally cylindrical, self-sustaining form has a diameter of less that about 19 mm, said tampon having an absorbent capacity as measured by the syngyna test of between about 9 to about 12 grams, said tampon being fluid expanding, and said tampon having an expanded width upon fluid absorption of at least about 24 mm.

2. The absorbent tampon of claim 1 wherein the difference between said absorbent material diameter and said tampon expanded width is at least about 8 mm.

3. The absorbent tampon of claim 2 wherein the difference between said absorbent material diameter and said tampon expanded width is at least about 12 mm.

4. The absorbent tampon of claim 1 wherein said mass of absorbent material is subjected to microwave radiation during formation of said tampon.

5. An absorbent tampon comprising:
a mass of absorbent material which has been compressed into a generally cylindrical, self-sustaining form, wherein said tampon has an absorbent capacity as measured by the syngyna test of between about 9 grams and about 12 grams, and wherein said tampon demonstrates a rate of expansion as measured by the expansion under pressure test from time zero until two minutes of at least about 1.6 mm/min.

6. An absorbent tampon comprising:
a mass of absorbent material which has been compressed into a generally cylindrical, self-sustaining form, wherein said tampon has an absorbent capacity as measured by the syngyna test of between about 9 grams and about 12 grams, and wherein said tampon demonstrates a rate of expansion as measured by the expansion under pressure test from time zero until seven minutes of at least about 0.82 mm/min.

* * * * *